United States Patent [19]

Lang et al.

[11] Patent Number: 5,529,905
[45] Date of Patent: Jun. 25, 1996

[54] METHOD OF ASSAYING PLASMA PROTEINS WITH PROTHROMBIN FRAGMENTS

[75] Inventors: Hartmut Lang; Berta Moritz, both of Vienna, Austria

[73] Assignee: Immuno Aktiengesellschaft, Vienna, Austria

[21] Appl. No.: 351,736

[22] Filed: Dec. 8, 1994

Related U.S. Application Data

[63] Continuation of Ser. No. 61,387, May 14, 1993, abandoned.

[30] Foreign Application Priority Data

May 15, 1992 [AT] Austria .................................. 1000/92

[51] Int. Cl.$^6$ .............. C12Q 1/56; G01N 31/00; C07K 1/00
[52] U.S. Cl. .................. 435/13; 435/4; 435/810; 436/16; 436/18; 436/69; 436/808; 530/380; 530/381; 530/382; 530/383; 530/384
[58] Field of Search ............................ 435/13, 4, 810, 435/968, 975; 436/16, 18, 69, 504, 808; 530/380, 381, 382, 383, 384

[56] References Cited

U.S. PATENT DOCUMENTS

| 4,496,653 | 1/1985 | Lill et al. ............................ 435/7 |
| 5,187,102 | 2/1993 | Stocker et al. ....................... 436/69 |

FOREIGN PATENT DOCUMENTS

| 0420332 | 4/1991 | European Pat. Off. . |
| 9207954 | 5/1992 | WIPO . |

OTHER PUBLICATIONS

Doyl et al, *The Journal of Biological Chemistry*, vol. 265, No. 18, pp. 10693–10701, Jun. 1990.

Andersson, *Haemostasis*, vol. 1, pp. 31–43, 1972.

Lang et al, *Chemical Abstracts*, vol. 117, p. 424, Ref. #146756g, 1992.

Wreding et al, *J. Clin. Chem. Clin. Biochem.*, vol. 27, pp. 57–63, 1989.

Lofgen, *Arch. Gynecol*, vol. 226, pp. 17–21, 1978.

Sasahi et al, *Chemical Abstracts*, vol. 93, P. 428, Ref. #234584r, 1980.

Tijburg, Pim N. M. et al., "Formation of Meizothrombin as Intermediate in Factor Xa–catalyzed Prothrombin Activation on Endothelial Cells", *The Journal of Biological Chemistry*, vol. 266, No. 6, pp. 4017–4022 (Feb. 25, 1991).

Briet, E. et al., "Cleavage and Activation of Human Prothrombin by Echis Carinatus Venom", *Chemical Abstracts*, vol. 98, No. 3, p. 250 (Jan. 17, 1983) Columbus, Ohio, US; Abstract No. 13567.

Axen et al., "Chemical Coupling of Peptides and Proteins to Polysaccharides by Means of Cyanogen Halides," *Nature*, vol. 214, pp. 1302–1304 (Jun. 1967).

Stocker et al., "Preparation and Partial Ccharacterization of Bovine and Human Meizothrombin," *Journal of the International Society on Thrombosis and Haemostasis*, vol. 65, No. 6, pp. 645–1417 (Jun. 1991).

Stocker, "Laboratory Use of Hirudin," *Seminars in Thrombosis and Hemostasis*, vol. 17, No. 2, pp. 113–121 (1991).

*Primary Examiner*—Christina Y. Chan
*Assistant Examiner*—Abdel A. Mohamed
*Attorney, Agent, or Firm*—Foley & Lardner

[57] ABSTRACT

There is disclosed the use of prothrombin fragments, preferably of human prothrombin fragments, having a thrombin-like activity, in particular of meizothrombin, meizo thrombin (desF1), or mixtures thereof, for diagnostic purposes for assaying thrombin substrates as well as a reagent containing these prothrombin fragments.

21 Claims, No Drawings

METHOD OF ASSAYING PLASMA PROTEINS WITH PROTHROMBIN FRAGMENTS

This application is a continuation of application Ser. No. 08/061,387, filed May 14, 1993, now abandoned.

BACKGROUND OF THE INVENTION

The invention relates to a new use of prothrombin fragments, in particular, of meizothrombin, meizothrombin (desF1), or mixtures thereof.

The determination of thrombin substrates by activation by means of thrombin constitutes an important methodology of characterizing blood and plasma products. Thus, concentrations or activities of fibrinogen, factor V, factor VIII or protein C, for instance, are normally determined by activation by means of thrombin in plasma-containing samples.

Thrombin is a 36 kD protein that plays a leading role in the blood coagulation cascade, its main function being the transformation of fibrinogen to fibrin, the latter forming a fibrin network by aid of factor XIII also activated by thrombin.

Moreover, thrombin also activates blood coagulation factors, such as factor V, factor VIII and protein C, causing the aggregation of thrombocytes. A number of other proteins, such as fibronectin, thrombospondin and apolipoprotein, various collagens, aminin, etc. (cf. Table 1 in Stocker, Sem. Thr. Hem. 17 (2) p. 114 (1991)) likewise can be cleaved by thrombin. In the following description, such proteins are denoted as "thrombin substrates".

On account of its important position in the coagulation cascade, the action of thrombin in vivo is very precisely controlled by activity effectors or inhibitors.

However, in particular, these inhibitors interfere with the assaying of thrombin substrates, because the inhibitors falsify the results in a sample, or a much larger, excessive amount of thrombin must be added prior to assaying in order to outplay the inhibitors present.

An important thrombin inhibitor, for instance, is heparin in combination with antithrombin III. Heparin practically is contained in any blood sample, either if blood donations are heparinized, i.e., admixed with heparin, immediately after having been taken to prevent premature coagulation or if the patient has obtained heparin, e.g., in an anticoagulation therapy.

The thrombin-inhibiting agent proper is antithrombin III. Heparin potentiates the effect of antithrombin III.

In a heparin-containing blood or plasma sample, there is always the risk of getting falsified results in thrombin concentration, thrombin substrate activation or kinetic assays, unless it has previously been freed from heparin in a cumbersome manner or heparin has been neutralized.

This involves an additional process step, which is hardly advantageous in diagnostic methods to be feasible in as simple a manner as possible for purposes of routine. Any additional process step not only involves higher operational expenditures, but also constitutes a potential additional error source of the assaying process.

Thrombin is formed in blood from an inactivated precursor protein, i.e., prothrombin, to a mature enzyme via several intermediate steps. The mature enzyme consists of two chains (A and B chains) interconnected by a disulfide bridge.

Meizothrombin or meizothrombin (desF1) are prothrombin fragments of this type, having been formed by the incomplete activation of prothrombin to thrombin (cf. FIG. 1 in Doyle et al., J. Biol. Chem. 265 (18), 10693–10701 (1990)). Meizothrombin (desF1) is formed by the activation of prothrombin in the absence of a thrombin inhibitor. In doing so, meizothrombin is first formed, which is proteolytically degraded to meizothrombin (desF1) after cleavage of the fragment F1. Thus, the molecular weight is reduced from approximately 72 kD to approximately 48 kD. These fragments are said to be instable, because they degrade autocatalytically, meizothrombin, for instance, being rapidly transformed into α-thrombin by autocatalysis. Meizothrombin and meizothrombin (desF1) also may be produced by the action of the snake venom ecarin on thrombin.

Experiments carried out by Doyle et al. have demonstrated that, in contrast to prothrombin, bovine meizothrombin has a protease activity that is very low as compared to that of thrombin.

Although meizothrombin is capable of cleaving, e.g., fibrinogen into fibrin, or of activating protein C at a low rate, it is not inhibited by heparin, or the inibition effect is smaller by orders of magnitude (Stocker & Müller, Thrombosis and Haemostasis 65 (6), Abstract 855 (1991). However, it has also been shown that human prothrombin fragments are substantially more instable than, for instance, bovine ones.

But it is also known that some snake venoms cleave thrombin substrates. Andersson (Haemostasis 1, 31–43 (1972)) describes a thrombin-like activity of several snake venoms, expressing the same in NIH units/ml analogous to thrombin. However, the use of snake venoms within the scope of diagnostics by human proteins has the disadvantage of inspecific interactions (intraspecies interactions). Therefore, efforts have been made to use only mammal proteins, preferably human proteins, particularly in the development of diagnostic methods for the determination of human factors. An essential prerequisite for an assaying method is the unambiguous reaction of the proteins used.

SUMMARY OF THE INVENTION

The invention is based on the object of providing a new use of prothrombin fragments, avoiding error sources caused by inhibitors. By this, the invention is to provide for a simple and precise method of assaying thrombin substrates.

Thus, the object of the invention is the use of prothrombin fragments, preferably human prothrombin fragments, having a thrombin-like activity, in particular, of meizothrombin, meizothrombin (desF1) or mixtures thereof, for diagnostic purposes for assaying thrombin substrates.

It has been shown that these fragments are also capable of cleaving substrates that may be reacted by thrombin. Thrombin-like activity in this context means protease activity capable of cleaving thrombin substrates whose reaction kinetics and reaction parameters, such as pH or ionic strength optimums, inhibitors, effectors, allosteric interactions, etc. need not necessarily be identical with those of thrombin, though.

The use according to the invention offers the advantage that the thrombin-like activity of the substances mentioned is heparin-insensitive on account of their low affinity for antithrombin III compared to thrombin activity. Diagnostic assays using the plasma proteins mentioned, thus, are independent of the heparin content of a sample and, thus, may be realized in a simple manner. In accomplishing these and other objectives, herein is provided a method of assaying plasma proteins in a test sample comprising the steps of:

(A) adding prothrombin fragments which have thrombin-like activity to said test sample to form an admixture, wherein conditions in said admixture permit activation of plasma proteins in said admixture by said prothrombin fragments; and (B) evaluating said admixture for effects of activated plasma proteins. The prothrombin fragments of the above method may comprise meizothrombin, meizothrombin (desF1), mixtures thereof, and the like.

There is also provided a modification to the above method wherein plasma proteins activatable by said prothrombin fragments are added to said admixture during step (A), resulting in activated plasma proteins, and said conditions permit said activated plasma proteins to interact with other plasma proteins in said admixture.

Additionally, there is provided a test kit comprising (A) prothrombin fragments having a thrombin-like activity and (B) a vessel for containing a test sample with said prothrombin fragments. The test kit may also further comprise a detection reagent, an activatable plasma protein, phospholipids, a thrombin substrate or $Ca^{2+}$ ions. Typically, detection reagents interact with either the activated thrombin substrates or with substances that interact with the activated thrombin substrates. These detection reagents may comprise chromogenic reagents, radiolabeled substances such as antibodies, and the like. Representative chromogenic reagents include S 2238 and S 2222 from Kabi and Immunochrome FVIII:C® from Immuno AG.

In addition, there is provided a test reagent comprising (A) prothrombin fragments having a thrombin-like activity and (B) a detection reagent. The test reagent may further comprise an activatable plasma protein, phospholipids, a thrombin substrate, and $Ca^{2+}$ ions.

Accordingly, thrombin substrates, such as fibrinogen, factor V, factor VIII, factor XIII and protein C, may be determined directly by activation with a reagent containing the prothrombin fragments mentioned.

According to the invention, not only thrombin substrates may be determined, but also substances that interact in any manner with thrombin substrates activated in accordance with the invention.

Thus, the reagent can be used for the indirect determination of factors of the coagulation cascade via activated thrombin substrates. Factor VIII may, for instance, be admixed to a reagent and activated in situ. Thereby, the determination of factor IX and, moreover, of factor X have become possible.

As a result, the invention also relates to the use of prothrombin fragments, preferably human prothrombin fragments, having a thrombin-like activity, in particular, of meizothrombin, meizothrombin (desF1) or mixtures thereof, for the activation of thrombin substrates followed by the assaying of a plasma protein interacting with the activated thrombin substrate directly or indirectly. Other objects, features and advantages of the present invention will become apparent from the following detailed description, tables and data.

DETAILED DESCRIPTION OF PREFERRED EMBODIMENTS

In accordance with the invention, meizothrombin or meizothrombin (desF1), preferably human meizothrombin or meizothrombin (desF1), are used either separately or in mixtures. These substances may be provided in a standardized manner, for instance, by controlled cleavage, using snake venoms, etc., wherein it has surprisingly been shown that they exhibit sufficient stability necessary for diagnostics.

Proteins produced by way of gene technology, which exhibit an activity similar to that of thrombin on account of their structures and have a lower affinity for antithrombin III than thrombin, are suitable for the use according to the invention.

The invention, furthermore, comprises a reagent containing prothrombin fragments, preferably human prothrombin fragments, having thrombin-like activity, in particular, meizothrombin, meizothrombin (desF1) or mixtures thereof, to be used for diagnostic purposes for assaying thrombin substrates and activating thrombin substrates followed by the determination of a plasma protein directly or indirectly interacting with the activated thrombin substrate, for instance, proteins of the coagulation cascade, such as factor Xa and factor Va.

Reagents containing the prothrombin fragments mentioned and used in accordance with the invention, if desired, have been lyophilized, optionally further containing an activatable thrombin substrate to be used for diagnostic purposes.

The invention also may comprise a reagent which further comprises one or several plasma proteins that may be activated, $Ca^{2+}$-ions and, if desired, phospholipids, or a reagent which further comprises a detection reagent.

Furthermore, a simple test kit can be produced, which comprises a detection reagent in addition to the reagents claimed.

The test kit contains at least a reagent comprising prothrombin fragments having a thrombin-like activity, in particular meizothrombin, meizothrombin (desF1) or mixtures thereof, or a reagent comprising prothrombin fragments having a thrombin-like activity, in particular meizothrombin, meizothrombin (desF1) or mixtures thereof, which additionally contains one or several plasma proteins that may be activated, and a detection reagent, and preferably may additionally contain a thrombin substrate.

The choice of the detection method and, thus, the detection reagent, apparently depends on the nature of the substance to be assayed contained in the sample. The activity of activated protein C, for instance, is determined by the chromogenic substrate S 2238 (Kabi); it is possible to determine the coagulation time or to use labelled substances.

The invention will be explained in more detail by the following examples.

1. Preparation of meizothrombin and molecular weight distribution 1.1. Preparation of immobilized Ecarin Ecarin (Pentapharm) was bound to BrCN-activated Sepharose (Pharmacia) at a concentration of 250 U/ml gel according to the method by Axen et al. (1967).

1.2. Preparation of meizothrombin 1 ml gel was incubated with 4 U prothrombin (from plasma, purified by adsorption on DEAE-Sephadex and subsequently additional chromatographic purification) in an 0.02 M Na-acetate buffer, 0.15 M NaCl, pH 5.2, for 1 hour at room temperature. Then, the product was separated from the gel by filtration.

1.3. Molecular weight distribution

After native SDS-PAGE and immunoblotting (1st antibody: anti-F.II, polyclonal from rabbit; 2nd antibody: peroxidase-conjugated anti-rabbit antibody from goat) the molecular weight distribution was determined and quantification was carried out. The product has the following molecular weight distribution; thrombin like activity: 67 to 75 kD (31%, 45 to 50 kD (40%); moreover, it was found: > 100 kD (7%), 32 to 38 kD (13%), < 20 kD (9%).

Reference: Axen R., Porath A. R., Ernback J. S., Nature 214, 1392–1404, 1967.

2. Determination of fibrinogen 2.1. Coagulation time of normal plasma 1 ml lyophilized normal plasma (Reference Plasma 100%; Immuno) was dissolved in 1 ml water with or without the addition of heparin (0; 0.3; 0.6; 1.0 and 2.0 U/ml). 200 µl of the plasma were incubated at 37° C. for 2 min. After this, coagulation was triggered with 200 µl of a solution of 5.8 NIH-analogous U/ml meizothrombin, prepared according to 1., or with 3.3 U/ml or 10.0 NIH-U/ml thrombin (Thrombin Reagent, Immuno). The time until clot formation was measured by a Schnitger-Gross coagulometer (Amelung). From Table 1, it is apparent that the coagulation time of the thrombin formulations is extended by the heparin content of the sample, while the action of meizothrombin is hardly affected by heparin.

|  | Coagulation time(s) Heparin content of sample (U/ml) | | | | |
| --- | --- | --- | --- | --- | --- |
|  | 0 | 0.3 | 0.6 | 1.0 | 2.0 |
| Thrombin (NIH-U/ml) | | | | | |
| 3.3 | 16.1 | 96.1 | >400 | >400 | >400 |
| 10 | 7.0 | 15.6 | 67.4 | >400 | >400 |
| Meizothrombin (NIH-analogous U/ml) | | | | | |
| 5.8 | 5.5 | 6.1 | 7.6 | 8.0 | 8.6 |

2.2 Reference curve for fibrinogen

Lyophilized normal plasma (cf. 2.1) was dissolved by 1 ml distilled water with and without the addition of diverse thrombin inhibitors (1 U/ml each of antithrombin III, heparin or antithrombin III/heparin complex (Atheplex®, Immuno)) and was diluted with 0.1 M phosphate buffer (pH 7.5) to different concentrations. From these, 100 µl sample were mixed with 50 µl of the same buffer and incubated at 37° C. for 2 min. After the addition of 150 µl of a solution of 10.5 NIH-analogous U/ml meizothrombin (Pentapharm) or 5 NIH-U/ml thrombin (Thrombin Reagent, Immuno) the coagulation time was determined in a manner analogous to 2.1.

|  | Inhibitor addition | | | |
| --- | --- | --- | --- | --- |
|  | No inhib. | Atheplex | ATIII | Heparin |
| Coagulation time with thrombin(s) | | | | |
| Sample conc'd | 17.1 | >300 | >350 | >300 |
| 1:2 | 21.6 | 61.6 | >350 | 50.4 |
| 1:4 | 27.6 | 37.1 | 101.6 | 36.1 |
| 1:8 | 41.6 | 38.6 | 54.6 | 48.9 |
| Coagulation time with meizothrombin(s) | | | | |
| Sample conc'd | 15.1 | 16.0 | 19.7 | 25.5 |
| 1:2 | 23.6 | 26.6 | 28.8 | 31.6 |
| 1:4 | 34.6 | 36.6 | 37.1 | 39.1 |
| 1:8 | 56.1 | 57.6 | 54.0 | 60.6 |

3. Meizothrombin in a diagnostic agent as activator of the coagulation cascade

Factor VIII in normal plasma (cf. 2.1) was activated by meizothrombin produced according to 1. (0; 3 or 5 U/ml) upon addition of 0; 1; 2; 5 or 10 U heparin/ml, and was assayed indirectly via factor Xa and chromogenic substrate. To this end, the assay Immunochrom FVIII:C® (Immuno AG) was used according to the manufacturer's instructions, meizothrombin having been added to reagent A and reagent B having been used without polybren. This assay contains thrombin, thus enabling the direct comparison of meizothrombin and thrombin to determine active coagulation factors in the assay system. The following Table demonstrates that the activation and determination of factor VIII is less influenced by the heparin content of the plasma in the presence of meizothrombin.

| Heparin (U/ml) Meizothrombin (NIH-analogous U/ml) | 0 | 1 | 2 | 5 | 10 |
| --- | --- | --- | --- | --- | --- |
|  | | | Color development (%) | | |
| 0 | 100 | 99 | 95.6 | 80 | 52.1 |
| 3 | 100 | 99 | 97.4 | 87.8 | 73.3 |
| 5 | 100 | 100 | 98 | 92.2 | 80.1 |

It is to be understood that the above description and specific examples, while indicating preferred embodiments of the invention, are given by way of illustration only, because various changes and modifications within the spirit and scope of the invention will become apparent to those skilled in the art from the discussion and disclosure herein.

What we claim is:

1. A method of assaying a test sample for a procoagulant protein that is a substrate of thrombin, comprising the steps of:

(A) adding at least one prothrombin fragment selected from the group consisting of meizothrombin and meizothrombin (desF1) to said test sample to form an admixture, wherein said prothrombin fragment activates said procoagulant protein to form an activated procoagulant protein; and (B) evaluating said admixture for effects of said activated procoagulant protein.

2. A method according to claim 1, wherein coagulation time is measured in step (B).

3. A method according to claim 1, wherein said prothrombin fragment is of human origin.

4. A method according to claim 1, wherein said procoagulant protein is selected from the group consisting of fibrinogen, factor V, factor VIII, and factor XIII.

5. A method according to claim 1, wherein step (B) employs a detection reagent to detect said activated procoagulant protein.

6. A method according to claim 5 wherein said detection reagent is selected from the group consisting of a chromogenic substrate and a radiolabeled substance.

7. A test kit for assaying a test sample for a procoagulant protein that is a substrate of thrombin comprising (A) at least one prothrombin fragment selected from the group consisting of meizothrombin and meizothrombin (desF1); (B) a detection reagent; and (C) a vessel for containing said test sample with said prothrombin fragment.

8. A test kit according to claim 7, further comprising phospholipids and $Ca^{2+}$ ions.

9. A test kit according to claim 7 further comprising a thrombin substrate.

10. A test kit according to claim 7, wherein said fragment is of human origin.

11. A test kit according to Claim 7, further comprising an activatable plasma protein.

12. A test kit according to claim 11, wherein said activatable plasma protein is factor VIII.

13. A test reagent for assaying a plasma protein comprising (A) at least one prothrombin fragment selected from the group consisting of meizothrombin and meizothrombin (desF1); and (B) a detection reagent.

14. A test reagent according to claim 13, further comprising phospholipids and $Ca^{2+}$ ions.

15. A test reagent according to claim 13, further comprising a thrombin substrate.

16. A test reagent according to claim 13, wherein said prothrombin fragment is of human origin.

17. A test reagent according to claim 13, further comprising an activatable plasma protein.

18. A test reagent according to claim 17, wherein said activatable plasma protein is factor VIII.

19. A method of assaying a plasma protein in a test sample, comprising the steps of:

(A) adding to said test sample (i) at least one prothrombin fragment selected from the group consisting of meizothrombin and meizothrombin (desF1) and (ii) a procoagulant protein that is different from said plasma protein and activatable by said prothrombin fragment, wherein said prothrombin fragment activates said procoagulant protein to form an activated procoagulant protein that can have an effect on said plasma protein, (B) determining whether said activated procoagulant protein of step (A) has had an effect on said plasma protein.

20. A method according to claim 19, wherein said effect of step (B) is detected with a detection reagent.

21. A method according to claim 19, wherein said procoagulant protein is factor VIII and said plasma protein is selected from the group consisting of factor IX and factor X.

* * * * *